United States Patent [19]

Koss

[11] Patent Number: 4,960,131
[45] Date of Patent: Oct. 2, 1990

[54] PENIS ERECTION TESTING AND MEASURING DEVICE

[76] Inventor: Walter Koss, Industriestrasse, D-6222 Geisenheim/Rhein, Fed. Rep. of Germany

[21] Appl. No.: 183,524

[22] Filed: Apr. 19, 1988

Related U.S. Application Data

[63] Continuation of Ser. No. 491,270, May 4, 1983, abandoned.

[30] Foreign Application Priority Data

May 6, 1982 [DE] Fed. Rep. of Germany ... 8213060[U]

[51] Int. Cl.[5] ............................................. A61B 5/03
[52] U.S. Cl. .................................................... 128/774
[58] Field of Search ............. 128/774; 33/174 D, 179

[56] References Cited

U.S. PATENT DOCUMENTS

| | | |
|---|---|---|
| 947,879 | 2/1910 | Worstall ................................ 33/179 |
| 1,339,896 | 5/1920 | Kemper ................................ 33/179 |
| 1,857,523 | 5/1932 | Wittel .................................. 33/179 |
| 2,636,281 | 4/1953 | Unger .................................. 33/179 |
| 4,428,385 | 1/1984 | Morales ............................... 128/774 |
| 4,474,187 | 10/1984 | Timm et al. ...................... 128/77 R |

FOREIGN PATENT DOCUMENTS

| | | |
|---|---|---|
| 473394 | 3/1929 | Fed. Rep. of Germany ........ 33/179 |
| 2303266 | 11/1976 | France ................................ 33/179 |
| 8301574 | 5/1983 | PCT Int'l Appl. ................ 128/774 |

Primary Examiner—Max Hindenburg
Assistant Examiner—John P. Lacyk
Attorney, Agent, or Firm—Gifford, Groh, Sprinkle, Patmore and Anderson

[57] ABSTRACT

An erection testing and measuring device comprises a band having a slider secured to one end, with an aperture for receiving the other end of the band. The device is fitted around a penis to be tested and measured, in an unerected condition, expansion of the penis upon an erection occurring causing the band to be pulled through the slider member against a retarding force produced thereby.

26 Claims, 2 Drawing Sheets

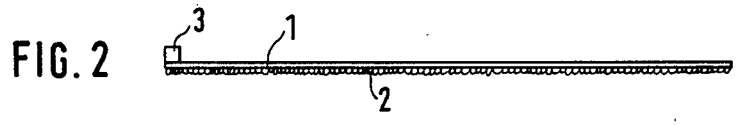
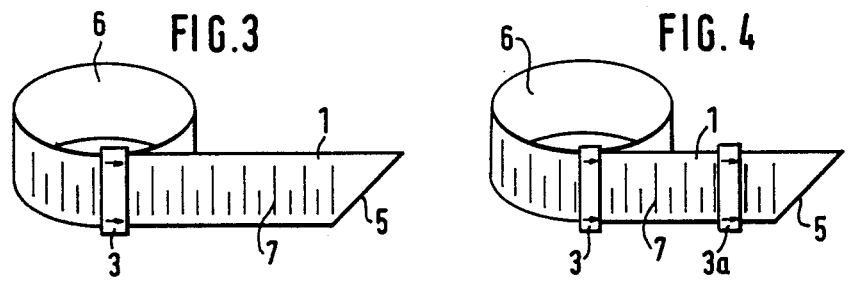
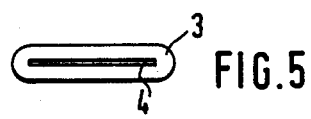
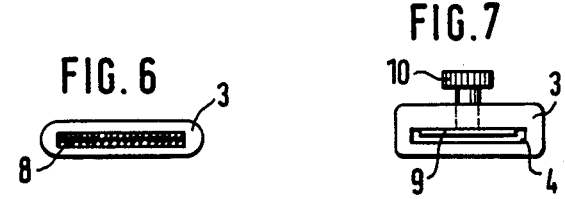
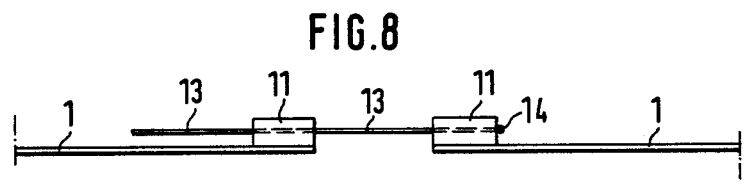
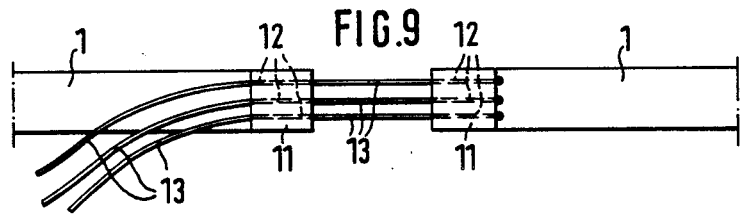
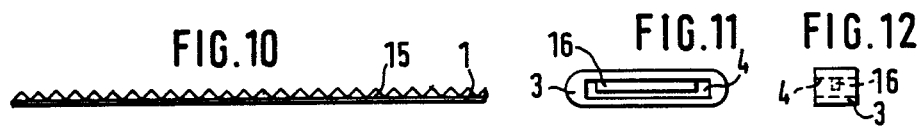

PENIS ERECTION TESTING AND MEASURING DEVICE

This is a continuation of co-pending application Ser. No. 491,270 filed on May 4, 1983, abandoned.

BACKGROUND OF THE INVENTION

Before investigating and treating problems with penis erection, it is necessary to find out whether a patient is in fact still having erections, and if so, what is the quality or the degree of erection when such occurs. For example, when a patient suffers from difficulties or problems in regard to erection, which are due to psychological reasons, it may happen that the patient experiences erections while asleep, although he himself knows nothing of such erections. In other cases however, before arriving at a decision as to whether for example it is appropriate or necessary to employ a penis prosthesis, it is necessary to carry out investigations into the quality of the erection achieved. That includes for example and in particular determining the increase in diameter or peripheral measurement of the penis, and also establishing the force with which such increase in penis size occurs, in order thereby to be able to arrive at conclusions concerning the degree of stiffness which is attained in the erected condition.

SUMMARY OF THE INVENTION

An object of the present invention is to provide a penis erection testing and measuring device which is simple and inexpensive.

Another object of the present invention is to provide a penis erection testing and measuring device which can be satisfactorily used by the patient himself without unpleasant effects and which can also be fitted to take erection measurements during the night or at other times while the patient is asleep.

Still another object of the present invention is to provide an erection testing and measuring device which provides reliable information and values in respect of the state of erection.

Yet another object of the present invention is to provide an erection testing and measuring device which can be readily set to given degrees of test sensitivity.

A further object of the invention is an erection testing and measuring device which is re-usable.

These and other objects are achieved by a penis erection testing and measuring device comprising a band which can be fitted to the shaft of the penis to be tested, in an encircling relationship therewith. Carried by or secured to one end of the band is a slider member which, with the other end of the band or an extension portion carried thereby, forms a braking or retardation means for preventing the band from being pulled without resistance through the slider member. The slider member has an opening for the band to extend therethrough, either with its other end or with the above-mentioned extension portion, and the latter may comprise for example one or more wire portions or one or more thread portions or like elongate portions on the actual end of the band itself.

The device can be fitted by the patient himself, encircling the penis when in a non-erect condition, in such a way that the band of the device snugly fits around the penis, but without causing strangulation or substantial constriction thereof. With the slider member in the appropriate position, as dictated by the circumferential dimension of the penis in the non-erect condition in which the device is fitted, a marking is then made on the band, or a scale value, where the band has scale markings thereon, in accordance with a preferred feature of the invention, is read off and possibly noted down. When an erection occurs, if the force which is produced and applied to the device by the penis is sufficient, the band or the end extension portion thereof will be pulled through the slider member, against the resistance exerted thereby. It is then possible, and possibly after the patient has woken up, to establish whether on the one hand any erection at all has taken place and if so, whether the force occurring was sufficient to overcome the sliding friction applied to the band by the slider member, and on the other hand, what increase in the peripheral dimension of the penis was achieved when it was in the erected condition. If the patient wakes up due to the pain caused by the band encircling the penis, then he can carry out a manual and visual check on the condition of the erection.

If a number of bands or slider members which produce a different retardation effect are used at the same time or in succession, it is then also possible to obtain information about the forces which are produced when an erection occurs. It is also possible for a number of devices to be simultaneously fitted to the penis in different positions thereon, for example under the glans and at the root, to make it possible to ascertain different supplies of blood to the various parts concerned. The measuring device may be used many times, but it may also be so simple and inexpensive that a fresh device can be used for each patient.

In an advantageous feature of the device according to this invention, the slider member may be in the form of a flat loop-like member having a slot therethrough, for the band to extend through the slot, the width of the slot substantially corresponding to the width of the band. In that device, with the band being of a given nature and thickness the width or the height of the slot will determine the band retardation force, by virtue of the ends or sides of the slot co-operating with and rubbingly bearing against the surface of the band, whereby the device can thus be easily adapted to the particular requirements of any situation. The loop-like member may be made from plastic material or from metal. It is only necessary to ensure that the width of the slot in the slider member does not alter unintentionally, which would have the effect of falsifying testing and measurement results.

If for example the doctor dealing with the patient wishes to measure different forces, the device may be so designed that the braking or retardation force applied to the band may be varied, for example by means of an adjusting screw which presses the limb portions of the loop-like slider member together under a spring force, or by means of a pressure plate which is disposed in the slot in the loop-like slider member and which is adjustable relative to the slider member by means of an adjusting screw, thereby to apply an adjustable force to the band where it passes through the slider member. In that case, the band may comprise a smooth plastic or metal band in order to produce reproducible retardation forces which do not vary even over long periods of time.

In a preferred embodiment of the device according to the present invention, the band may be a textile material of the tufted type or the type bearing woollen or like bundles or bunches on the surface thereof, with the loops of the tufting or bunching being closed loops. Such a band does not irritate the skin, on the one hand, while on the other hand, it produces a constant retardation force which is jerk-free and uniform when it is pulled through the slot in the slider member.

In accordance with another advantageous embodiment of the present invention, the end of the band which is remote from the end carrying the slider member has one or more elongate extension portions secured thereto, and the slider member has one or more apertures or bores extending therethrough in the direction of the band, with the extension portion or portions being passed through the one or more respective bores. The or each extension portion may be for example in the form of a wire, thread, yarn or like elongate portion. The material used for the band and the material used for the extension portion or portions may be selected independently of each other, and in such a way as to adapt them to the respective functions to be performed thereby. The sliding friction caused by the extension portion or portions in their respective bores may be adjusted to different values, as desired. For example, in that case, the position of the extension portions or threads may be so adjusted that, in the initial movement of enlargement of the circumferential dimension of the penis, a first thread or yarn which produces a slight retardation effect is pulled through the bore in which it is received, and then a further thread or yarn producing a higher retardation effect is tensioned and pulled through its bore, and so on, to provide a progressive increase in the resistance force applied to the movement of the band.

In a further advantageous embodiment, the band may be provided with a tooth arrangement which defines a plurality of recesses in the surface of the band, which extend substantially transversely with respect to the longitudinal direction of the band, while the slot or opening in the slider member is provided therein with one or more resilient projections such as ribs, boss members or like portions, which co-operate with the tooth arrangement on the band, to give a ratchet-like action. That permits the force required to pull the band through the slider member to be reliably adjusted. In this case also, the band, together with the slider member and the projections therein, are particularly suitable for manufacture in one piece from plastic material. It will be appreciated however that the other embodiments referred to herein may also be manufactured in one piece in the same way.

In all the embodiments of the present invention, it is possible for the force required to pull the band through the slider member, or the retardation force applied to the band by the slider member, to be increased by the provision of one or more slider members which can be fitted on to the free end of the band or the above-mentioned extension portion thereof. It will be appreciated therefore that the additional slider member or members is or are loose, in the sense of not being connected to the band, otherwise than by simply being fitted thereonto. When the loose slider members are arranged on the band at a certain spacing from the slider member fixed on the first end thereof, and at spacings from each other, where a plurality of such further slider members are employed, it is possible to produce a given gradation in the retardation force, after a respective given increase in circumferential dimension of the penis has occurred.

Further objects, features and advantages of devices in accordance with the principles of the present invention will be apparent from the following detailed description thereof and the accompanying drawings.

BRIEF DESCRIPTION OF THE DRAWINGS

FIG. 1 shows a plan view of a first embodiment of a device according to the present invention, FIG. 2 shows a side view of the FIG. 1 embodiment, FIG. 3 shows a perspective view of the embodiment shown in FIGS. 1 and 2, when put into loop form, FIG. 4 shows the embodiment of FIGS. 1 through 3, with the incorporation of an additional, loose slider member on the band, FIG. 5 shows a front view of the slider member used in the device illustrated in FIGS. 1 through 4, FIG. 6 shows a modified form of the FIG. 5 slider member, FIG. 7 shows a slider member with means for producing an adjustable retardation force on the band, FIG. 8 shows a side view of a second embodiment of the device according to the present invention, FIG. 9 shows a plan view of the FIG. 8 embodiment, FIG. 10 shows a side view of the band of a third embodiment of the device according to the invention, FIG. 11 shows a front view of the slider member of the FIG. 10 embodiment, and FIG. 12 shows a side view of the FIG. 11 slider member;

FIG. 13 shows a modified form of the FIG. 5 slider member; and

FIG. 14 shows a side view of another embodiment of the device according to the present invention.

DESCRIPTION OF PREFERRED EMBODIMENTS

Referring firstly to FIGS. 1 through 5, illustrated therein is a penis erection testing and measuring device comprising a strip or band 1 which is about 20 cm in length and about 2 cm in width. The band 1 comprises a suitable material, such as a textile material, as indicated, having a fleece or tufted layer on one surface of the band, as indicated at 2. The threads or yarns of the layer 2 form closed loops, such tufted textile configurations being known.

Provided on or at least substantially adjacent to one end of the band 1, on the surface thereof remote from the surface carrying the layer 2, is a slider member 3 illustrated in the form of a loop-like member, which is shown in front view in FIG. 5 to which reference will shortly be made. The slider member 3 is fixed to the band 1 by any suitable means, as by adhesive, or may be formed in one piece therewith.

Referring now therefore to FIG. 5, the slider member 3 has an opening in the form of a slot 4 which substantially corresponds to the width of the band 1 which, in use of the device, passes through the slider member 3. The other end of the band 1, namely the end remote from the end bearing the slider member 3, is inclined as indicated at 5 to facilitate passing the band 1 through the slot 4, so that the device then forms a loop configuration as indicated at 6 in FIGS. 3 and 4. The device will thus be in that form, when it is fitted to a penis in an encircling relationship.

The tufted layer 2 on the band 1 ensures that the braking or retardation force which occurs when the band 1 is drawn through the slot 4 has and maintains a given value. That force may be easily determined, by virtue of the width of the slot 4.

In order to carry out an erection testing or measuring operation, the device is put into the loop form indicated at 6 in FIGS. 3 and 4, around the penis when in a non-erect condition, and then pulled tight until the band bears lightly against the penis. The position of the slider member relative to the band 1 is then read off on a scale 7 on the band 1, or marked by means of a marking put on the band 1 adjacent the slider member 3. When an erection occurs, the band 1 is then drawn through the slot 4, as the length of the loop encircling the penis increases as a result of the expansion due to the erection. In order for the band 1 to be drawn through the slot 4 in the slider member, the braking or retardation force applied to the band 1 must be overcome, thereby also giving information as to the force which has at least occurred, due to the penis going into an erect condition. Two forms of the device, which may desirably be distinguished by virtue of being of different colours, may have for example retardation or extension forces of 250 g and 450 g respectively.

If appropriate, the retardation force of any given device may be subsequently increased, in accordance with the illustration shown in FIG. 4, by fitting a further slider member 3a on to the free end of the band 1, the further slider member 3a not being secured to any part of the band, unlike the slider member 3 which is secured to the first end of the band. The increased retardation force occurs immediately if the further slider member 3a is pushed on to the band in such a position as to bear against the first slider member 3. However, as illustrated in FIG. 4, the slider member 3a may also be arranged at a certain spacing from the slider member 3. In that case, the increased retardation force will occur only after a certain degree of erection, sufficient to cause initial expansion of the loop 6 and thus movement of the slider member 3 along the band towards the slider member 3a, thereby providing information about the force occurring, from that point onward. If desired, it would also be possible to fit a plurality of additional slider members 3a on the band 1.

Reference will now be made to FIG. 6 showing a modified form of the slider member 3 in which the slot therein is lined with a tufted or bunch-bearing material 8, for example similar to the material forming the layer 2 on the band 1 shown in FIG. 1. In this case, in order to produce a properly defined retardation force, it is also possible to use a comparatively smooth band of plastic or textile material, or metal.

FIG. 7 shows another modified form of the slider member 3. Disposed in the slot 4 defined by the loop-like configuration of the slider member 3 is a pressure plate which can be varied in its position in the slot 4 by means of an adjusting screw 10 which is screw-threaded in one of the side limb portions of the loop member 3, thereby permitting the pressure applied to the band 1 by the pressure plate 9, and therefore also the retardation force, to be suitably adjusted in that manner. The adjusting screw may also be so arranged as to press the side limb portions of the loop slider member 3 together in order to adjustably grip the band in the slot.

Reference will now be made to FIGS. 8 and 9 showing another embodiment of the device which also comprises a band 1 which is formed into a loop, in a similar manner to the loop configuration shown in FIGS. 3 and 4. Accordingly, the dash-dotted vertical lines in FIGS. 8 and 9, on respective sides thereof, indicate that the band 1 is carried round to join to itself, to constitute a single band. Disposed on the two ends of the band 1 are respective blocks 11 of elastomeric plastic material, being secured thereon for example by adhesive. Each of the blocks 11 has three bores 12 extending therethrough in the longitudinal direction of the band 1, while wires or threads or like elongate extension portions 13 are passed through respective ones of the bores 12 in the blocks 11. The portions 13 are secured by knots 14 at their right-hand ends, so that they cannot be pulled through the block 11 on the right-hand side in FIGS. 8 and 9. The elongate portions 13 comprise for example monofilaments of plastic material. The dimensions of the bores 12 and the portions 13 are such that a predetermined braking or retardation force occurs when the ends of the band 1 and thus the blocks 11 are pulled apart. The braking resistances exerted by the three threads 13 may be different from one thread to another, to permit gradation in the resistance applied to movement of the band. The band 1 may again be a textile band, but it may also be a band of plastic material which is produced in one piece with the blocks 11, as by an injection moulding process. The portions 13 do not necessarily have to be of circular cross-section, and similarly in regard to the bores 12. Thus, it is possible to use other cross-sectional configurations, as well as modified strip-like configurations.

Referring now to FIGS. 10 through 12, illustrated therein is a device comprising a band 1 which has a plurality of recesses on one surface thereof, being defined in the illustrated construction by teeth 15 extending substantially transversely with respect to the longitudinal direction of the band 1. The band 1 is again passed through the slot 4 defined by a loop-like slider member 3. Disposed within the slot 4 is a resilient projection 16 in the form of a rib or limb portion, which co-operates with the teeth 15 in a ratchet-like manner. When therefore the band 1 is drawn through the gap 4, the projection 16 produces a brief detent action after each tooth 15. A given pulling force which defines the retardation effect is then necessary in order to pull the band 1 further on to the next tooth 15. The slider member 3 with the projection 16, which may be of a different configuration from that illustrated, are desirably made from a resilient plastic material of high resiliency, for example a polyacetal resin, known under the trade mark Delrin. However, it is also possible to use a metal slider member with a steel spring member fitted therein.

It will be seen therefore that the testing and measuring device as described above is simple, inexpensive and easy to manufacture, and can be re-used as often as desired, although, because of the low cost of production, it is readily possible for each patient to have a fresh testing device for his use.

The edges of the slot in the slider member may be rounded (FIG. 13), to enhance the reliability of measurement of the device, by permitting the band to move smoothly through the slider, while the inside surfaces of the slot may be roughened or of a non-smooth nature, in order to apply resistance to movement of the band through the slider. In addition, the thickness of the band may increase over its length, as for example in FIG. 14, to progressively increase the resistance to movement of the band through the slider, with suitable calibration of the scale 7 on the band.

Various modifications and alterations may be made in the above-described embodiments without thereby departing from the spirit and scope of the present invention.

I claim:

1. A device for testing and measuring the extent and the force of penis erection, comprising a band having first and second ends which is adapted to be fitted on the shaft of the penis in an encircling relationship therewith; a slider member secured to said first end of said band which insertably receives said second end of said band therethrough, so that said band encircles the penis; and means for retarding the sliding movement of said band through said slider member; wherein said retarding means provides a predetermined resistance to said sliding movement corresponding to a specific force of penis expansion.

2. A device as set forth in claim 1 wherein said slider member is in the form of a loop, and said retarding means comprises a slot in said slider for said band to pass therethrough, the width of said slot substantially corresponding to the width of said band.

3. A device as set forth in claim 2 wherein said slot has edges which are rounded.

4. A device as set forth in claim 2 wherein said slot has at least one non-smooth inside surface co-operable with said band.

5. A device as set forth in claim 4 wherein said at least one inside surface is roughened.

6. A device as set forth in claim 4 wherein said at least one inside surface has a projection thereon, co-operable with said band.

7. A device as set forth in claim 2 wherein the slot has at least one inside surface having a friction-enhancing material secured thereto.

8. A device as set forth in claim 7 wherein said material is a tufted textile material.

9. A device as set forth in claim 2 wherein said retarding means further comprises an adjusting screw carried by said loop member which is adapted to vary the retardation force applied to said band.

10. A device as set forth in claim 9 wherein said retarding means comprises a pressure plate disposed in said slot operatively connected to said screw and adapted to apply said retardation force to said band.

11. A device as set forth in claim 1 wherein said band is a smooth plastic band.

12. A device as set forth in claim 1 wherein said band is a smooth metal band.

13. A device as set forth in claim 1 wherein said band is a textile band having a closed-loop tufted means thereon.

14. A device as set forth in claim 1 wherein the thickness of said band increases over the length thereof.

15. A device as set forth in claim 1 wherein said slider member has at least one aperture therethrough and wherein said second end of said band comprises at least one elongated extension portion which is passed through said associated at least one aperture.

16. A device as set forth in claim 15 wherein said extension portion comprises thread.

17. A device as set forth in claim 15 wherein said extension portion comprises wire.

18. A device as set forth in claim 1 wherein said slider member and said band are made in one piece from plastic material.

19. A device as set forth in claim 1 wherein at least one further slider member is disposed displaceably against a resistance on said band between the first-mentioned slider member and said second end of said band.

20. A device as set forth in claim 1 wherein said band has a scale thereon.

21. A device as set forth in claim 13 wherein said band has opposing sides, and wherein said slider member is affixed to one side of said band and said tufted means is disposed on the other side of said band.

22. A device for measuring and testing the extent and the force of penis expansion, comprising:
a band having first and second ends, and being dimensioned to encircle the shaft of said penis;
a slider member secured to said first end of said band, said second end of said band being insertably received through said slider member; and
means for measuring both the extent and the force of penis expansion comprising means for retarding the sliding movement of said band in said slider member by providing a predetermined amount of resistance to said sliding movement corresponding to a specific force of penis expansion.

23. A method of testing and measuring the extent and the force of penis erection, comprising the steps of:
snugly fitting the device as set forth in claim 1 in an encircling relationship about the shaft of said penis, while said penis is in a nonerect condition, without substantial constriction of said penis;
allowing said device to remain about said penis a sufficient time for an erection to normally occur; and
observing said device after said time to determine whether said band has moved with respect to said slider member, thereby determining whether the force of any such erection was sufficient to overcome said predetermined resistance, and determining the extent of any such erection.

24. A device for testing and measuring penis erection, comprising a band having first and second ends which is adapted to be fitted on the shaft of the penis in an encircling relationship therewith; a slider member secured to said first end of said band which insertably receives said second end of said band therethrough, so that said band encircles the penis; and means for retarding the sliding movement of said band through said slider member; wherein said slider member has at least one aperture therethrough and said second end of said band comprises at least one elongated extension portion which is passed through said associated at least one aperture; and wherein said slider member has a plurality of bores extending therethrough, said extension portion comprises a wire extending through each of said bores, and the sliding friction of the wires in their respective bores varies from one wire to another.

25. A device for testing and measuring penis erection, comprising a band having first and second ends which is adapted to be fitted on the shaft of the penis in an encircling relationship therewith; a slider member secured to said first end of said band which insertably receives said second end of said band therethrough, so that said band encircles the penis; and means for retarding the sliding movement of said band through said slider member; wherein said slider member has at least one aperture therethrough and said second end of said band comprises at least one elongated extension portion which is passed through said associated at least one aperture; and wherein said slider member has a plurality of bores extending therethrough, said extension portion comprises a thread extending through each of said bores, and the sliding friction of the threads in their respective bores varies from one thread to another.

26. A device for testing and measuring penis erection, comprising a band having first and second ends which is adapted to be fitted on the shaft of the penis in an encircling relationship therewith; a slider member secured to said first end of said band which insertably receives said second end of said band therethrough, so that said band encircles the penis; and means for retarding the sliding movement of said band through said slider member; wherein said slider member is in the form of a loop, and said retarding means comprises a slot in said slider for said band to pass therethrough, the width of said slot substantially corresponding to the width of said band; and wherein said band has a surface providing a plurality of recesses extending transversely with respect to the lengthwise direction of said band, and at least one resilient projection is disposed in said slot and is adapted ratchet-like to co-operate with said recesses.

* * * * *